(12) United States Patent
Ikemoto et al.

(10) Patent No.: US 7,038,042 B2
(45) Date of Patent: May 2, 2006

(54) PROCESS FOR PRODUCING CYCLIC COMPOUND

(75) Inventors: Tomomi Ikemoto, Takarazuka (JP); Tatsuya Ito, Kashiba (JP); Kiminori Tomimatsu, Minoo (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 36 days.

(21) Appl. No.: 11/010,215

(22) Filed: Dec. 10, 2004

(65) Prior Publication Data

US 2005/0096475 A1 May 5, 2005

Related U.S. Application Data

(63) Continuation of application No. 10/204,315, filed as application No. PCT/JP01/01190 on Feb. 20, 2001, now Pat. No. 6,864,367.

(30) Foreign Application Priority Data

Feb. 21, 2000 (JP) ............................. 2000/048929

(51) Int. Cl.
*C07D 487/00* (2006.01)
*C07C 313/00* (2006.01)
(52) U.S. Cl. ...................... 540/461; 549/355
(58) Field of Classification Search ............... 540/476, 540/461; 560/125; 549/355
See application file for complete search history.

(56) References Cited

U.S. PATENT DOCUMENTS

| 4,952,573 | A | 8/1990 | LeClerc et al. |
| 5,886,197 | A | 3/1999 | Hirose et al. |
| 6,369,110 | B1 | 4/2002 | Kitano et al. |

FOREIGN PATENT DOCUMENTS

| DE | 42 39 000 | 5/1994 |
| EP | 1 184 381 | 3/2002 |
| EP | 1 211 239 | 5/2002 |
| WO | WO 98/55475 | 10/1998 |
| WO | WO 99/61414 | 2/1999 |
| WO | WO 00/76993 A1 | 12/2000 |
| WO | WO 01/10826 A1 | 2/2001 |
| WO | WO 01/17947 A1 | 3/2001 |
| WO | WO 01/17971 A1 | 3/2001 |

OTHER PUBLICATIONS

Reinhoudt et al, Journal of American Chemical Society, Reactivity of Cis-Fused 3-(Dialkylamino)cyclobutenes in Polar and Apolar Solvents. Synthesis, X-ray +Structures, and Reactions of cis,cis- and cis,trans-1,3-Cycloalkadienes, 1984, 106, pp. 1341-1350.*

Assy et al. "Synthesis of Thiopyrano[2,3-d]Pyrimidines and Thieno[2,3-d]Pyrimidines" *Polish J. Chem.* 69: 887-891 (1995).

Anzinl et al. "Novel, Potent, and Selective 5-HT3 Receptor Antagonists Based on the Arylpiperazine Skeleton: Synthesis, Structure, Biological Activity, and Comparative Molecular Field Analysis Studies" *J. Med. Chem.* 1995; 38:2692-2704.

Eskola et al. "Medium-Ring Systems, 6. Synthesis and Isomerizations of Medium-ring 3-Methylenecycloalkanones and 3-Methylcycloalkenones" *J. Org. Chem.* 1997; 62: 5732-5742.

Watanabe et al. "A Convenient Method for the Synthesis of D1,6-Bicyclo[4.n.0]alken-2-ones" *Tetrahedron Letters* 40 (1999) 8133-8136.

(Continued)

*Primary Examiner*—Paul A. Zucker
(74) *Attorney, Agent, or Firm*—Elaine M. Ramesh; Mark Chao

(57) ABSTRACT

A process suitable for safely mass-producing, through a short step, cyclic compounds useful in medicines, agricultural chemicals, foods, cosmetics, and chemical products or as intermediates therefor. The process, which is for producing a compound represented by the formula:

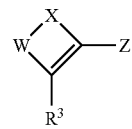

{wherein Z represents an electron-attracting group; W represents optionally substituted ethylene or optionally substituted vinylene; $R^3$ represents hydrogen or an optionally substituted hydrocarbon group; and X represents a divalent group [provided that when W represents optionally substituted vinylene, then —X—$CH_2$-Z is not —$X^1$—$X^2$—$CH_2$-Z (wherein $X^1$ represents sulfur or optionally substituted nitrogen and $X^2$ represents optionally substituted ethylene)]} or a salt thereof, is characterized by subjecting a compound represented by the formula (II) or a salt thereof:

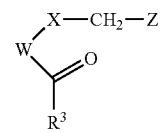

(wherein the symbols have the same meanings as the above) to a ring closure reaction in a solvent containing a carbonic diester.

2 Claims, No Drawings

OTHER PUBLICATIONS

Beccalli et al. "A New Synthesis of Cyclodecane- and Cycloundecane-1,3-dione" *J. Org. Chem.* 1981; 46: 222-223.

Mariano et al. "The Chemistry of Azocines. Intermediates for the Synthesis of Pyrrolizidines" *J. Org. Chem.* vol. 42(17): 2903-2910 (1977).

Lamm et al. "Ring-expansion of Some Sulfur-containing Heterocyclic Compounds with Dimethyl Acetylenedicarboxylate" *Acta Chemica Scandinavia B36* (1982) 435-442.

Kawahara et al. "Synthesis of 1-Acyl-1,2-Dihydro-1-Benzazocine Derivatives" *Heterocycles,* vol. 16(5) 729-731 (1981).

Acheson and Paglietti "Addition Reactions of Heterocyclic Compounds. Part 76. Aminopropylbenzenecarboxylic Esters and Tetrahydroazocines from Tetrahydropyridines and Acetylenic Esters" *J. Chem Res.* (S) 1981, p. 306.

Thies, R., et al. "A Ring Expansion Route to Benzo Substituted Medium- and Large-Ring Systems, Synthesis of trans-7,8-Benzocyclododeca-5,7-dien-1-one", *Journal of Organic Chemistry,* (1977) vol. 42, No. 2, pp. 280-281.

Database Crossfire Beilstein (Online) Beilstein Institute zur Forderung der Chemischen Wissenschaften, Frankfurt am Main, DE, compounds with Beilstein RN: 6969264 & Bull. CHem. Soc., Jpn.; EN, 59, 7, 1986, pp. 2317-2320.

Database Crossfire Beilstein (Online) Beilstein Institute zur Forderung der Chemischen Wissenschaften, Frankfurt am Main, DE, compounds with Belstein RN: 6209258 & J. Am. Chem. Soc., EN, 109, 15, 1987, pp. 4723-4726.

Database Crossfire Beilstein (Online) Beilstein Institute zur Forderung der Chemischen Wissenschaften, Frankfurt am Main, DE, compounds with Beilstein RN: 5049939 & Liebigs Ann. Chem. GE, 8, 1983, pp. 1374-1392.

Database Crossfire Beilstein (Online) Beilstein Institute zur Forderung der Chemischen Wissenschaften, Frankfurt am Main, DE, compounds with Beilstein RN: 1637344 & J. Am. Chem. Soc., EN, 96, 1974, pp. 1193-1197.

Database Crossfire Beilstein (Online) Beilstein Institute zur Forderung der Chemischen Wissenschaften, Frankfurt am Main, DE, compounds with Beilstein RN: 6192950 & J. Am. Chem. Soc., EN, 110, 19, 1988, pp. 6536-6541.

Database Crossfire Beilstein (Online) Beilstein Institute zur Forderung der Chemischen Wissenschaften, Frankfurt am Main, DE, compounds with Beilstein RN: 503562 & J. Chem. Soc., EN, 1965, pp. 3200-3206.

* cited by examiner

PROCESS FOR PRODUCING CYCLIC COMPOUND

This application is a continuation of U.S. patent application Ser. No. 10/204,315, filed Aug. 19, 2002, now U.S. Pat. No. 6,864,367, issued Mar. 8, 2005, which was the National Phase filing of International Patent Application No. PCT/JP01/01190, filed Feb. 20, 2001.

TECHNICAL FIELD

The present invention relates to a process for producing cyclic compounds useful as medicines, agricultural chemicals, foods, cosmetics and chemical products, or intermediates thereof.

BACKGROUND ART

Heretofore, several synthetic methods for cyclic compounds have been described in literature, including, for example, (1) an intramolecular Friedel-Crafts Reaction in the case of cyclic ketone derivatives (JP-A 57-192379, etc.), (2) a Dieckmann-type cyclization reaction of diester derivatives, followed by reduction and dehydration reactions in the case of cyclic acrylic acid derivatives (J. Chem. Res., Synop., (1987), (12), 394–5, etc.), (3) an intramolecular Wittig Reaction in the case of cyclic alkene derivatives (WO98/55475, etc.) and others.

However, even though a variety of useful intermediates have been described, for example, in J. Heterocyclic Chem., 31, 351–355 (1994), Heterocycles, 49, 215–232 (1998), J. Heterocyclic Chem., 33, 1909–1913 (1996), etc., cyclic compounds (especially, cyclic compounds having 8- or more-membered ring) are still generally difficult to synthesize and can be obtained only at low yields even if possible.

From the current situation as described above, it is desirable to establish a convenient production method (i.e., a production method which employs readily available low-cost raw materials, and reagents suitable for large scale synthesis and having no disposal problems, and which comprises relatively short steps and is easier to carry out), of cyclic compounds, especially cyclic alkene derivatives, which can be easily converted to a variety of derivatives including, e.g., cyclic ketone derivatives or cyclic acrylic acid derivatives, due to their characteristic chemical structure.

DISCLOSURE OF INVENTION

As a result of intensive studies, the present inventors found that a cyclic alkene derivative can be produced inexpensively and conveniently by using an activated methylene derivative as a reaction intermediate and by conducting a cyclization reaction in the presence of a carbonic diester, and on the basis of this knowledge, after further studies, completed the present invention.

That is, the present invention provides (1) A process for producing a compound represented by the formula:

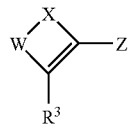

[wherein, Z is an electron-withdrawing group; W is an optionally substituted ethylene or an optionally substituted vinylene, and when the ethylene or the vinylene has two substituent groups, said substituent groups may be bound to each other to form an optionally substituted cyclic ring; $R^3$ is a hydrogen atom or an optionally substituted hydrocarbon group; and X is a divalent group (preferably, a divalent group having 3 or more atoms in the straight-chain moiety thereof) (however, when W is an optionally substituted vinylene, —X—CH$_2$-Z is not —X$^1$—X$^2$—CH$_2$-Z (wherein, $X^1$ is a sulfur atom or an optionally substituted nitrogen atom, $X^2$ is an optionally substituted ethylene))] or a salt thereof, which comprises subjecting a compound represented by the formula:

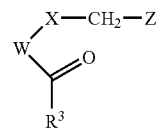

[wherein, each symbol has the same meaning described as above] or a salt thereof to a cyclization reaction in a solvent containing a carbonic diester;

(2) The process according to the above-mentioned (1), wherein X is a divalent group having 1 to 12 atoms in the straight-chain moiety thereof (preferably, 3 to 12 atoms in the straight-chain moiety thereof);

(3) The process according to the above-mentioned (1), wherein Z is a carboxyl group which is esterified;

(4) The process according to the above-mentioned (1), wherein $R^3$ is a hydrogen atom;

(5) The process according to the above-mentioned (1), which comprises the reaction being carried out in the presence of a base;

(6) The process according to the above-mentioned (5), wherein the base is an alcoholate;

(7) The process for producing a compound represented by the formula:

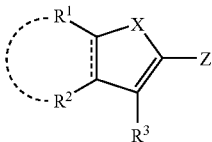

[wherein, Z is an electron-withdrawing group; $R^1$ and $R^2$ each are a hydrogen atom, a halogen atom, an optionally substituted amino group, an optionally substituted hydroxy group, an optionally substituted thiol group, an optionally substituted hydrocarbon group, or an optionally substituted heterocyclic; $R^1$ and $R^2$ may be bound to each other to form an optionally substituted ring; $R^3$ is a hydrogen atom or an optionally substituted hydrocarbon group; the combined line of a broken line and a solid line is a single bond or a double bond; and X is a divalent group (preferably, a divalent group having 3 or more atoms in the straight-chain moiety thereof) (however, when the combined line of a broken line and a solid line is a double bond, —X—CH$_2$-Z is not —X$^1$—X$^2$—CH$_2$-Z (wherein, X$^1$ is a sulfur atom or an optionally substituted nitrogen atom, X$^2$ is an optionally substituted ethylene))] or a salt thereof, which comprises subjecting a compound represented by the formula:

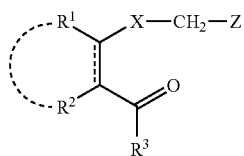

[wherein, each symbol has the same meaning described as above] or a salt thereof to a cyclization reaction in a solvent containing a carbonic diester;

(8) The process according to the above-mentioned (7), wherein X is a divalent group having 1 to 12 atoms in the straight-chain moiety thereof (preferably, 3 to 12 atoms in the straight-chain moiety thereof);

(9) The process according to the above-mentioned (7), wherein Z is a carboxyl group which is esterified;

(10) The process according to the above-mentioned (7), wherein R$^3$ is a hydrogen atom;

(11) The process according to the above-mentioned (7), which comprises the reaction being carried out in the presence of a base;

(12) The process according to the above-mentioned (11), wherein the base is an alcoholate;

(13) The process for producing a compound represented by the formula:

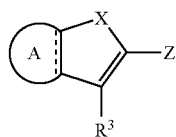

[wherein, Z is an electron-withdrawing group; R$^3$ is a hydrogen atom or an optionally substituted hydrocarbon group; the combined line of a broken line and a solid line is a single bond or a double bond; ring A is an optionally substituted ring; and X is a divalent group (preferably, a divalent group having 3 or more atoms in the straight-chain moiety thereof) (however, when the ring A is an optionally substituted benzene ring and the combined line of a broken line and a solid line is a double bond, —X—CH$_3$-Z is not —X$^1$—X$^2$—CH$_2$-Z (wherein, X$^1$ is sulfur atom or an optionally substituted nitrogen atom; X$^2$ is an optionally substituted ethylene))] or a salt thereof, which comprises subjecting a compound represented by the formula:

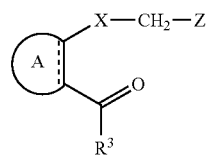

[wherein, each symbol has the same meaning described as above] or a salt thereof to a cyclization reaction in a solvent containing a carbonic diester;

(14) The process according to the above-mentioned (13), wherein X is a divalent group having 1 to 12 atoms in the straight-chain moiety thereof (preferably, 3 to 12 atoms in the straight-chain moiety thereof);

(15) The process according to the above-mentioned (13), wherein Z is a carboxyl group which is esterified;

(16) The process according to the above-mentioned (13), wherein R$^3$ is a hydrogen atom;

(17) The process according to the above-mentioned (13), which comprises the reaction being carried out in the presence of a base;

(18) The process according to the above-mentioned (17), wherein the base is an alcoholate;

(19) The compound represented by the formula:

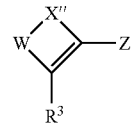

[wherein, Z is an electron-withdrawing group; W is an optionally substituted ethylene or an optionally substituted vinylene, and when the ethylene or the vinylene has two substituent groups, said substituent groups may be bound to each other to form an optionally substituted ring; R$^3$ is a hydrogen atom or an optionally substituted hydrocarbon group; and X" is a divalent group having 4 or more atoms in the straight-chain moiety thereof] or a salt thereof;

(20) The compound according to the above-mentioned (19), wherein X" is a divalent group having 4 to 6 atoms in the straight-chain moiety thereof;

(21) The compound according to the above-mentioned (19), wherein Z is a carboxyl group which is esterified;

(22) The compound according to the above-mentioned (19), wherein R$^3$ is a hydrogen atom;

(23) The compound represented by the formula:

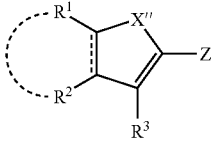

[wherein, Z is an electron-withdrawing group; R$^1$ and R$^2$ each are a hydrogen atom, a halogen atom, an optionally substituted amino group, an optionally substituted hydroxy group, an optionally substituted thiol group, an optionally substituted hydrocarbon group or an optionally substituted heterocyclic group; $R^1$ and $R^2$ may be bound to each other to form an optionally substituted ring; $R^3$ is a hydrogen atom or an optionally substituted hydrocarbon group; the combined line of a broken line and a solid line is a single bond or a double bond; and X" is a divalent group having 4 or more atoms in the straight-chain moiety thereof] or a salt thereof;

(24) The compound according to the above-mentioned (23), wherein X" is a divalent group having 4 to 6 atoms in the straight-chain moiety thereof;

(25) The compound according to the above-mentioned (23), wherein Z is a carboxyl group which is esterified;

(26) The compound according to the above-mentioned (23), wherein $R^3$ is a hydrogen atom;

(27) The compound represented by the formula:

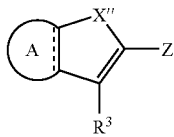

[wherein, Z is an electron-withdrawing group; $R^3$ is a hydrogen atom or an optionally substituted hydrocarbon group; the combined line of a broken line and a solid line is a single bond or a double bond; ring A is an optionally substituted ring; and X" is a divalent group having 4 or more atoms in the straight-chain moiety thereof] or a salt thereof;

(28) The compound according to the above-mentioned (27), wherein X" is a divalent group having 4 to 6 atoms in the straight-chain moiety thereof;

(29) The compound according to the above-mentioned (27), wherein Z is a carboxyl group which is esterified; and

(30) The compound according to the above-mentioned (27), wherein $R^3$ is a hydrogen atom; and the like.

Examples of "electron-withdrawing group" used in the present specification include (i) a carboxyl group which may be optionally esterified or amidated, (ii) a group represented by the formula: —(CO)$R^4$ (wherein, $R^4$ is a hydrogen atom or an optionally substituted hydrocarbon group), (iii) nitrile group, (iv) nitro group, (v) a group represented by the formula: —(SO$_m$)$R^5$ (wherein, m is an integer of 1 or 2, and $R^5$ is an optionally substituted hydrocarbon group), (vi) a group represented by the formula: —P$R^6R^7$ (wherein, $R^6$ and $R^7$ each are an optionally substituted hydrocarbon group), (vii) a group represented by the formula: —(PO)(O$R^8$)(O$R^9$) (wherein, $R^8$ and $R^9$ each are a hydrogen or an optionally substituted hydrocarbon group), (viii) an optionally substituted aryl group, (ix) an optionally substituted alkenyl group, (x) a halogen atom (e.g., fluorine, chlorine, bromine, iodine, etc.) and (xi) a nitroso group and the like, preferably, a carboxyl group which may be optionally esterified or amidated, a group represented by the formula: —(CO)$R^4$, nitrile group, nitro group, a group represented by the formula: —(SO$_m$)$R^5$, a group represented by the formula: —P$R^6R^-$, a group represented by the formula: —(PO)(O$R^6$)(O$R^9$), more preferably, a carboxyl group which is esterified (e.g., a carboxyl group which is esterified by a $C_{1-4}$ alkyl such as methoxycarbonyl, ethoxycarbonyl, t-butoxycarbonyl, etc.) and the like.

The "carboxyl group which is esterified" in the "carboxyl group which may be optionally esterified or amidated" of (i) above include a group represented by the formula: —(CO)O$R^{10}$ (wherein, $R^{10}$ is an optionally substituted hydrocarbon group), while the "carboxyl group which is amidated" include a group represented by the formula: —(CO)N$R^{11}R^{12}$ (wherein, $R^{11}$ and $R^{12}$ are, respectively, a hydrogen atom or an optionally substituted hydrocarbon group, and $R^{11}$ and $R^{12}$ may be bound to each other to form a 5- to 7-membered (preferably, 5- to 6-membered) cyclic amino group together with a neighboring nitrogen atom (e.g., tetrahydropyrrole, piperazine, piperidine, morpholine, thiomorpholine, pyrrole, imidazole, etc.)).

Further, in the formula of (vi) or (vii) above, $R^6$ and $R^7$, or $R^8$ and $R^9$ may be bound to each other to form, for example, a lower ($C_{2-6}$) alkylene (e.g., dimethylene, trimethylene, tetramethylene, etc.), a lower ($C_{2-6}$) alkenylene (e.g., —CH$_2$—, —CH=CH—, —CH$_2$—CH$_2$—CH=CH—, —CH$_2$—CH=CH—CH$_2$—, etc.), or a lower ($C_{4-6}$) alkadienylene (e.g., —CH=CH—CH=CH—, etc.), etc., preferably, a lower ($C_{1-6}$) alkylene, more preferably, a lower ($C_{2-4}$) alkylene, and these divalent groups may have optionally substituent groups including, for example, hydroxy group, a halogen atom, a $C_{1-4}$ alkyl, a $C_{1-4}$ alkoxy, etc.

Examples of the "aryl group" in the optionally substituted aryl group of (viii) above include, for example, $C_{6-14}$ aryl groups such as phenyl, naphthyl, etc., preferably, $C_{6-10}$ aryl groups, etc., more preferably, phenyl, etc. The aryl group may have 1 to 3 substituent groups similar to those of the "optionally substituted hydrocarbon group" described below.

The "alkenyl groups" in the optionally substituted alkenyl group of (ix) above include, for example, alkenyl groups having 2 to 10 carbon atoms such as vinyl, allyl, crotyl, 2-pentenyl, 3-hexenyl, etc., and the like, preferably, lower ($C_{2-6}$) alkenyl groups, etc., more preferably, vinyl, etc. The alkenyl group may have 1 to 3 substituent groups similar to those of the "optionally substituted hydrocarbon group" described below.

Examples of the "hydrocarbon group" in the "optionally substituted hydrocarbon group" used in the present specification include;

(1) an alkyl group (e.g., $C_{1-10}$ alkyl groups such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably, lower ($C_{1-6}$) alkyl groups, etc.);

(2) a cycloalkyl group. (e.g., $C_{3-7}$ cycloalkyl groups such as cyclopropyl, cyclobutyl, cyclopentyl, cyclohexyl, cycloheptyl and the like);

(3) an alkenyl group (e.g., alkenyl groups having 2 to 10 carbon atoms such as vinyl, allyl, crotyl, 2-pentenyl, 3-hexenyl, etc., preferably, lower ($C_{2-6}$) alkenyl groups, etc.);

(4) a cycloalkenyl group (e.g., cycloalkenyl groups having 3 to 7 carbon atoms such as 2-cyclopentenyl, 2-cyclohexenyl, 2-cyclopentenylmethyl, 2-cyclohexenylmethyl and the like);

(5) an alkynyl group (e.g., alkynyl groups having 2 to 10 carbon atoms such as ethynyl, 1-propynyl, 2-propynyl, 1-butynyl, 2-pentynyl, 3-hexynyl, etc., preferably, lower ($C_{2-6}$) alkynyl groups and the like);

(6) an aryl group (e.g., $C_{6-14}$ aryl groups such as phenyl, naphthyl, etc., preferably, $C_{6-10}$ aryl groups, more preferably, phenyl, etc.); and (7) an aralkyl group (e.g., phenyl-$C_{1-4}$ alkyl groups (e.g., benzyl, phenethyl, etc.) and the like). The examples of the hydrocarbon groups are preferably, an alkyl group, more preferably, a $C_{1-4}$ alkyl group such as methyl, ethyl, etc., and particularly preferably, methyl.

Said hydrocarbon group may have substituent groups, including, for example, a halogen atom (e.g., fluorine, chlorine, bromine, iodine, etc.), nitro, cyano, hydroxy, an optionally substituted thiol group (e.g., thiol, $C_{1-4}$ alkylthio, etc.), an optionally substituted amino group (e.g., amino, mono$C_{1-4}$ alkylamino, di$C_{1-4}$alkylamino, 5- to 6-membered cyclic amino groups such as tetrahydropyrrole, piperazine, piperidine, morpholine, thiomorpholine, pyrrole, imidazole and the like), a carboxyl group which may be optionally esterified or amidated (e.g., carboxyl, $C_{1-4}$ alkoxycarbonyl, carbamoyl, mono$C_{1-4}$alkylcarbamoyl, di$C_{1-4}$ alkylcarbamoyl, etc.), a $C_{1-4}$ alkyl group which may be optionally substituted with halogen atoms or $C_{1-4}$ alkoxy groups (e.g., trifluoromethyl, methyl, ethyl, etc.), a $C_{1-4}$ alkoxy group which may be optionally substituted with halogen atoms or $C_{1-4}$ alkoxy groups (e.g., methoxy, ethoxy, trifluoromethoxy, trifluoroethoxy, etc.), formyl, a $C_{2-4}$ alkanoyl group (e.g., acetyl, propionyl, etc.), a $C_{1-4}$ alkylsulfonyl group (e.g., methanesulfonyl, ethanesulfonyl, etc.), and a $C_{1-4}$ alkylsulfinyl (e.g., methanesulfinyl, ethanesulfinyl, etc.). The number of the substituent groups is preferably 1 to 3.

In the formula above, the "ethylene" and the "vinylene" in the "optionally substituted ethylene" and the "optionally substituted vinylene" represented by W include divalent groups represented by the formula: —$CH_2$—$CH_2$— and the formula: —CH═CH—. These divalent groups may have substituent groups at any position where substitution is possible, and examples thereof include substituent groups similar to those of "a halogen atom", "an optionally substituted amino group", "an optionally substituted hydroxy group", "an optionally substituted thiol group", "an optionally substituted hydrocarbon group" and "an optionally substituted heterocyclic group" represented by $R^1$ and $R^2$ described below. When the ethylene or the vinylene has two substituent groups, the substituent groups may be bound to each other to form an optionally substituted ring. Further, $R^1$ and $R^2$ may be bound to each other to form an optionally substituted ring. Here, examples of the optionally substituted ring are those similar to an optionally substituted ring as ring A described below (preferably, an optionally substituted benzene ring and the like).

Examples of the "halogen atom" represented by $R^1$ and $R^2$ in the formula above include fluorine, chlorine, bromine, iodine, etc.

Examples of the "optionally substituted amino group" represented by $R^1$ and $R^2$ in the formula above include amino groups which may be optionally substituted by the "optionally substituted hydrocarbon groups" mentioned above. The number of substituent groups may be any of 0 to 2. When two substituent groups are present, the two substituent groups may be the same or different. Further, the two substituent groups may be bound to each other to form a 5- to 7-membered (preferably, 5- to 6-membered) cyclic amino group together with neighboring nitrogen atoms (e.g., tetrahydropyrrole, piperazine, piperidine, morpholine, thiomorpholine, pyrrole, imidazole, etc.).

Examples of the "optionally substituted hydroxy group" represented by $R^1$ and $R^2$ in the formula above include hydroxy groups which may be optionally substituted by the "optionally substituted hydrocarbon groups" mentioned above.

Examples of "the optionally substituted thiol group" represented by $R^1$ and $R^2$ in the formula above include thiol groups which may be optionally substituted by the "optionally substituted hydrocarbon groups" mentioned above.

In the formula above, examples of the "heterocyclic ring" in the "optionally substituted heterocyclic group" represented by $R^1$ and $R^2$, include 5- to 7-memberd aromatic heterocyclic rings and saturated or non-aromatic heterocyclic rings (aliphatic heterocyclic rings), containing at least one (preferably, 1 to 4, more preferably 1 to 2) hetero atoms of 1 to 3 (preferably, 1 to 2) hetero atoms selected from the group consisting of oxygen atom, sulfur atom, nitrogen atom and other atoms.

Herein, examples of the "aromatic heterocyclic ring" include 5- to 6-membered aromatic monocyclic heterocyclic rings (e.g., furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine, etc.). Examples of the "non-aromatic heterocyclic ring" include 5- to 7-membered (preferably, 5- to 6-membered) saturated or unsaturated (preferably, saturated) non-aromatic heterocyclic rings (aliphatic heterocyclic rings) such as pyrrolidine, tetrahydrofuran, thiolane, piperidine, tetrahydropyran, morpholine, thiomorpholine, piperazine, pyran, etc., and 5- to 6-membered non-aromatic heterocyclic rings wherein all or a part of double bonds in the afore-mentioned aromatic monocyclic heterocyclic rings are saturated. The heterocyclic ring is preferably a 5- to 6-membered aromatic ring, and more preferably furan, thiophene, pyrrole, or pyridine (preferably a 6-membered ring).

Examples of substituent groups which may be possessed by the heterocyclic ring include substituent groups exemplified as the substituent groups on the "optionally substituted hydrocarbon group" described above, and the number of the substituent groups is 1 to 3.

In the formula above, Z is preferably an esterified carboxyl group, $R^3$ is preferably a hydrogen atom, and $R^1$ and $R^2$ each is preferably a hydrogen atom or an optionally substituted hydrocarbon group, more preferably a hydrogen atom, and it is also preferable that $R^1$ and $R^2$ are bound to each other to form an optionally substituted benzene ring.

The substituent groups which may be possessed by the "optionally substituted benzene ring" used in the present specification include substituent groups exemplified as the substituent groups on the "optionally substituted hydrocarbon group" described above; the afore-described "optionally substituted aryl groups", which may be bound via a spacer (e.g., a divalent group having 1 to 4 atoms in the straight-chain moiety thereof) (preferably, afore-described "optionally substituted aryl groups" which is directly bound), and particularly preferably electron-donating groups. The number of the substituent groups is 1 to 4.

Examples of the "spacer" are —$(CH_2)_a$— [a is an integer of 1 to 4 (preferably, an integer of 1 to 2)], —$(CH_2)_b$—X'— [b is an integer of 0 to 3 (preferably, an integer of 0 to 1), X' is an optionally substituted imino group (e.g., imino groups which may be substituted with lower ($C_{1-6}$) alkyl, lower ($C_{3-7}$) cycloalkyl, formyl, lower ($C_{2-7}$) alkanoyl, lower ($C_{1-6}$) alkoxy-carbonyl etc.), a carbonyl group, an oxygen atom or an optionally oxidized sulfur atom (e.g., —$S(O)_n$— (n is an integer of 0 to 2))], —CH═CH—, —C≡C—, —CO—NH—, —$SO_2$—NH— etc. (preferably —$(CH_2)_b$—X'—, more preferably —$CH_2$—O—). These groups may be bound to the "optionally substituted benzene ring" via-either the right or left bond, but they are bound to the "optionally substituted benzene ring" preferably via the right bond.

Examples of the ring formed by binding $R^1$ and $R^2$ and the "optionally substituted ring" represented by A in the formula above include 5- to 7-membered (preferably, 5- to 6-membered) saturated or unsaturated alicyclic hydrocarbons such as $C_{5-7}$ cycloalkanes (e.g., cyclopentane, cyclohexane, cycloheptane, etc.), $C_{5-7}$ cycloalkenes (e.g., 1-cyclopentene, 2-cyclopentene, 3-cyclopentene, 2-cylcohexene, 3-cylcohexene, etc.), and $C_{5-6}$ cycloalkadienes (e.g., 2,4-cyclopentadiene, 2,4-cyclohexadiene, 2,5-cyclohexadiene, etc); 6- to 14-membered aromatic hydrocarbons such as benzene, naphthalene, azulene, acenaphthylene, etc.; and 5- to 7-memberd aromatic heterocyclic rings and saturated or unsaturated non-aromatic heterocyclic rings (aliphatic heterocyclic rings) containing at least one (preferably, 1 to 4, more preferably 1 to 2) hetero atoms of 1 to 3 (preferably, 1 to 2) hetero atoms selected from the group consisting of oxygen atom, sulfur atom, nitrogen atom and other atoms.

Examples of the "aromatic heterocyclic ring" include 5- to 6-membered aromatic monocyclic heterocyclic rings (e.g., furan, thiophene, pyrrole, oxazole, isoxazole, thiazole, isothiazole, imidazole, pyrazole, 1,2,3-oxadiazole, 1,2,3-thiadiazole, 1,2,3-triazole, pyridine, pyridazine, pyrimidine, pyrazine, etc.), and examples of the "non-aromatic heterocyclic ring" include 5- to 7-membered (preferably 5- to 6-membered) saturated or unsaturated non-aromatic monocyclic heterocyclic rings (aliphatic heterocyclic rings) such as pyrrolidine, tetrahydrofuran, thiolane, piperidine, morpholine, thiomorpholine, tetrahydropyran, piperazine, pyran etc., or 5- to 6-membered non-aromatic heterocyclic rings wherein all or a part of the double bonds in the aforedescribed aromatic monocyclic heterocyclic rings are saturated.

Further, the ring formed by binding $R^1$ and $R^2$, and the "optionally substituted ring" represented by A in the formula above may form a fused ring wherein 2 to 3 (preferably, 2) monocyclic rings described above are condensed. Preferable examples of the fused ring include fused rings of two same or different heterocyclic rings (preferably, one heterocyclic ring and one aromatic heterocyclic ring, more preferably, two same or different aromatic heterocyclic rings); and fused rings of a heterocyclic ring and a homocyclic ring (preferably, a heterocyclic ring and a benzene ring, more preferably, an aromatic heterocyclic ring and a benzene ring). Specific examples of the fused ring include indole, benzothiophene, benzofuran, benzimidazole, imidazo[1,2-a]pyridine, quinoline, isoquinoline, cinnoline, etc.

The ring formed by binding $R^1$ and $R^2$, and the "optionally substituted ring" represented by A in the formula above is preferably a 5- to 6-membered aromatic ring, more preferably benzene, furan, thiophene, pyrrole, or pyridine (preferably, a 6-membered ring), and particularly preferably benzene.

The ring formed by binding $R^1$ and $R^2$, and the ring A may have substituent groups, examples thereof include those similar to the substituent groups which may be possessed by the "benzene ring" in the "optionally substituted benzene ring" described above. 1 to 3 same or different substituent groups may substitute at any position of the ring where substitution is possible.

In the formula above, the "divalent group" represented by X is preferably a divalent group having 3 or more atoms in the straight-chain moiety thereof, and, for example, any group may be employed whichever ring B in the following formula can form a 5- to 16-membered ring (preferably 5- to 12-membered ring, more preferably 7- to 10-membered ring, particularly preferably 8- to 10-membered ring): the formula

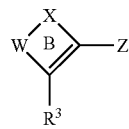

the formula

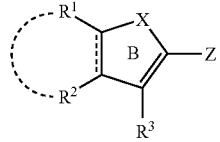

or the formula

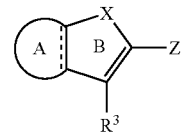

That is, X may be any of divalent groups having 1 to 12 atoms in the straight-chain moiety thereof (preferably 1 to 8, more preferably 3 to 6, and particularly preferably 4 to 6), and specific examples of the divalent group include (1) —$(CH_2)_{a1}$— (a1 is an integer of 1 to 12, preferably 3 to 12), —$(CH_2)_{a2}$—(CH=CH)—$(CH_2)_{a3}$— (a2 and a3 each are the same or different integer of 0 to 10. But, the sum of a2 and a3 is 10 or lower, preferably 1 to 10), —$(CH_2)_{a4}$—(CH=C=CH)—$(CH_2)_{a5}$— (a4 and a5 each are the same or different integer of 0 to 9. But, the sum of a4 and a5 is 9 or lower), (2) —$(CH_2)_{b1}$—Y—$(CH_2)_{b2}$— (b1 and b2 each are the same or different integer of 0 to 11. But, the sum of b1 and b2 is 11 or lower, preferably 2 to 11. Y is O, S, or NH), —$(CH_2)_{b3}$—Y—$(CH_2)_{b4}$—(CH=CH)—$(CH_2)_{b5}$— or —$(CH_2)_{b5}$—(CH=CH)—$(CH_2)_{b4}$—Y—$(CH_2)_{b3}$— (b3, b4 and b5 are, respectively, the same or different integer of 0 to 9. But, the sum of b3, b4 and b5 is 9 or less. Y is O, S, or NH), —$(CH_2)_{b6}$—Y—$(CH_2)_{b7}$—(CH=C=CH)—$(CH_2)_{b8}$— or —$(CH_2)_{b8}$—(CH=C=CH)—$(CH_2)_{b7}$—Y—$(CH_2)_{b6}$— (b6, b7, and b8 are, respectively, the same or different integer of 0 to 8. But, the sum of b6, b7 and b8 is 8 or less. Y is O, S, or NH), (3) —$(CH_2)_{c1}$—(N=CH)—$(CH_2)_{c2}$— (c1 and c2 are, respectively, the same or different integer of 0 to 10. But, the sum of c1 and c2 is 10 or less, preferably 1 to 10), —$(CH_2)_{c3}$—(N=CH)—$(CH_2)_{c4}$—(CH=CH)—$(CH_2)_{c5}$— or —$(CH_2)_{c5}$—(CH=CH)—$(CH_2)_{c4}$—(N=CH)—$(CH_2)_{c2}$— (c3, c4 and c5 are, respectively, the same or different integer of 0 to 8. But, the sum of c3, c4 and c5 is 8 or less), —$(CH_2)_{c6}$—(N=CH)—$(CH_2)_{c7}$—(CH=C=CH)—$(CH_2)_{c8}$— or —$(CH_2)_{c8}$—(CH=C=CH)—$(CH_2)_{c7}$—(N=CH)—$(CH_2)_{c6}$— (c6, c7 and c8 are, respectively, the same or different integer of 0 to 7. But, the sum of c6, c7 and c8 is 7 or less), (4) —$(CH_2)_{d1}$—(CH=N)—$(CH_2)_{d2}$— (d1 and d2 are, respectively the same or different integer of 0 to 10. But, the sum of d1 and d2 is 10 or lower, preferably 1 to 10), $-(CH_2)_{d3}-(CH=N)-(CH_2)_{d4}-(CH=CH)-(CH_2)_{d5}-$ or $-(CH_2)_{d5}-(CH=CH)-(CH_2)_{d4}-(CH=N)-(CH_2)_{d3}-$ (d3, d4 and d5 are, respectively, the same or different integer of 0 to 8. But, the sum of d3, d4 and d5 is 8 or less), $-(CH_2)_{d6}-(CH=N)-(CH_2)_{d7}-(CH=C=CH)-(CH_2)_{d8}-$ or $-(CH_2)_{d8}-(CH=C=CH)-(CH_2)_{d7}-(CH=N)-(CH_2)_{d6}-$ (d6, d7 and d8 are, respectively, the same or different integer of 0 to 7. But, the sum of d6, d7 and d8 is 7 or less), (5) $-(CH_2)_{e1}-(N=N)-(CH_2)_{e2}-$ (e1 and e2 are, respectively, the same or different integer of 0 to 10. But, the sum of e1 and e2 is 10 or less, preferably 1 to 10), $-(CH_2)_{e3}-(N=N)-(CH_2)_{e4}-(CH=CH)-(CH_2)_{e5}-$ or $-(CH_2)_{e5}-(CH=CH)-(CH_2)_{e4}-(N=N)-(CH_2)_{e3}-$ (e3, e4 and e5 are, respectively, the same or different integer of 0 to 8. But, the sum of e3, e4 and e5 is 8 or less), $-(CH_2)_{e6}-(N=N)-(CH_2)_{e7}-(CH=C=CH)-(CH_2)_{e8}-$ or $-(CH_2)_{e8}-(CH=C=CH)-(CH_2)_{e7}-(N=N)-(CH_2)_{e6}-$ (e6, e7 and e8 are, respectively, the same or different integer of 0 to 7. But, the sum of e6, e7 and e8 is 7 or less), (6) $-(CH_2)_{f1}-Y-(CH_2)_{f2}-(N=CH)-(CH_2)_{f3}-$ (f1, f2 and f3 are, respectively, the same or different integer of 0 to 9. But, the sum of f1, f2 and f3 is 9 or less. Y is O, S or NH), $-(CH_2)_{f3}-(N=CH)-(CH_2)_{f2}-Y-(CH_2)_{f1}-$ (f1, f2 and f3 are, respectively, the same or different integer of 0 to 9. But, the sum of f1, f2 and f3 is 9 or less, Y is O, S or NH), $-(CH_2)_{f4}-(CH=CH)-(CH_2)_{f5}-Y-(CH_2)_{f6}-(N=CH)-(CH_2)_{f7}-$ (f4, f5, f6 and f7 are, respectively, the same or different integer of o to 7. But, the sum of f4, f5, f6 and f7 is 7 or less. Y is O, S or NH), $-(CH_2)_{f8}-Y-(CH_2)_{f9}-(CH=CH)-(CH_2)_{f10}-(N=CH)-(CH_2)_{f11}-$ (f8, f9, f10 and f11 are, respectively, the same or different integer of 0 to 7. But, the sum of f8, f9, f10 and f11 is 7 or less. Y is O, S or NH), $-(CH_2)_{f12}-Y-(CH_2)_{f13}-(N=CH)-(CH_2)_{f14}-(CH=CH)-(CH_2)_{f15}-$ (f12, f13, f14 and f15 are, respectively, the same or different integer of 0 to 7. But, the sum of f12, f13, f14 and f15 is 7 or less), $-(CH_2)_{f7}-(N=CH)-(CH_2)_{f6}-Y-(CH_2)_{f5}-(CH=CH)-(CH_2)_{f4}-$ (f4, f5, f6 and f7 are, respectively, the same or different integer of 0 to 7. But, the sum of f4, f5, f6 and f7 is 7 or less. Y is O, S or NH), $-(CH_2)_{f11}-(N=CH)-(CH_2)_{f10}-(CH=CH)-(CH_2)_{f9}-Y-(CH_2)_{f8}-$ (f8, f9, f10 and f11 are, respectively, the same or different integer of 0 to 7. But, the sum of f8, f9, f10 and f11 is 7 or less. Y is O, S or NH), $-(CH_2)_{f15}-(CH=CH)-(CH_2)_{f14}-(N=CH)-(CH_2)_{f13}-Y-(CH_2)_{f12}-$ (f12, f13, f14 and f15 are, respectively, the same or different integer of 0 to 7. But, the sum of f12, f13, f14 and f15 is 7 or less), (7) $-(CH_2)_{g1}-Y-(CH_2)_{g2}-(CH=N)-(CH_2)_{g3}-$ (g1, g2 and g3 are, respectively the same or different integer of 0 to 9. But, the sum of g1, g2 and g3 is 9 or less. Y is O, S or NH), $-(CH_2)_{g3}-(CH=N)-(CH_2)_{g2}-Y-(CH_2)_{g1}-$ (g1, g2 and g3 are, respectively, the same or different integer of 0 to 9. But, the sum of g1, g2 and g3 is 9 or less. Y is O, S or NH), $-(CH_2)_{g4}-(CH=CH)-(CH_2)_{g5}-Y-(CH_2)_{g6}-(CH=N)-(CH_2)_{g7}-$ (g4, g5, g6 and g7 are, respectively, the same or different integer of o to 7. But, the sum of g4, g5, g6 and g7 is 7 or less. Y is O, S or NH), $-(CH_2)_{g8}-Y-(CH_2)_{g9}-(CH=CH)-(CH_2)_{g10}-(CH=N)-(CH_2)_{g11}-$ (g8, g9, g10 and g11 are, respectively, the same or different integer of 0 to 7. But, the sum of g8, g9, g10 and g11 is 7 or less. Y is O, S or NH), $-(CH_2)_{g12}-Y-(CH_2)_{g13}-(CH=N)-(CH_2)_{g14}-(CH=CH)-(CH_2)_{g15}-$ (g12, g13, g14 and g15 are, respectively, the same or different integer of 0 to 7. But, the sum of g12, g13, g14 and g15 is 7 or less), $-(CH_2)_{g7}-(CH=N)-(CH_2)_{g6}-Y-(CH_2)_{g5}-(CH=CH)-(CH_2)_{g4}-$ (g4, g5, g6 and g7 are, respectively, the same or different integer of 0 to 7. But, the sum of g4, g5, g6 and g7 is 7 or less. Y is O, S or NH), $-(CH_2)_{g11}-(CH=N)-(CH_2)_{g10}-(CH=CH)-(CH_2)_{g9}-Y-(CH_2)_{g8}-$ (g8, g9, g10 and g11 are, respectively, the same or different integer of 0 to 7. But, the sum of g8, g9, g10 and g11 is 7 or less. Y is O, S or NH), $-(CH_2)_{g15}-(CH=CH)-(CH_2)_{g14}-(CH=N)-(CH_2)_{g13}-Y-(CH_2)_{g12}-$ (g12, g13, g14 and g15 are, respectively, the same or different integer of 0 to 7. But, the sum of g12, g13, g14 and g15 is 7 or less), (8) $-(CH_2)_{h1}-Y-(CH_2)_{h2}-(N=N)-(CH_2)_{h3}-$ (h1, h2 and h3 are, respectively the same or different integer of 0 to 9. But, the sum of h1, h2 and h3 is 9 or less. Y is O, S or NH), $-(CH_2)_{h3}-(N=N)-(CH_2)_{h2}-Y-(CH_2)_{h1}-$ (h1, h2 and h3 are, respectively, the same of different integer of 0 to 9. But, the sum of h1, h2 and h3 is 9 or less. Y is O, S or NH), $-(CH_2)_{h4}-(CH=CH)-(CH_2)_{h5}-Y-(CH_2)_{h6}-(N=N)-(CH_2)_{h7}-$ (h4, h5, h6 and h7 are, respectively, the same or different integer of 0 to 7. But, the sum of h4, h5, h6 and h7 is 7 or less. Y is O, S or NH), $-(CH_2)_{h8}-Y-(CH_2)_{h9}-(CH=CH)-(CH_2)_{h10}-(N=N)-(CH_2)_{h11}-$ (h8, h9, h10 and h11 are, respectively, the same or different integer of 0 to 7. But, the sum of h8, h9, h10 and h11 is 7 or less. Y is O, S or NH), $-(CH_2)_{h12}-Y-(CH_2)_{h13}-(N=N)-(CH_2)_{h14}-(CH=CH)-(CH_2)_{h15}-$ (h12, h13, h14 and h15 are, respectively, the same or different integer of 0 to 7. But, the sum of h12, h13, h14 and h15 is 7 or less), $-(CH_2)_{h7}-(N=N)-(CH_2)_{h6}-Y-(CH_2)_{h5}-(CH=CH)-(CH_2)_{h4}-$ (h4, h5, h6 and h7 are, respectively, the same or different integer of 0 to7. But, the sum of h4, h5, h6 and h7 is 7 or less. Y is O, S or NH), $-(CH_2)_{h11}-(N=N)-(CH_2)_{h10}-(CH=CH)-(CH_2)_{h9}-Y-(CH_2)_{h8}-$ (h8, h9, h10 and h11 are, respectively the same or different integer of 0 to 7. But, the sum of h8, h9, h10 and h11 is 7 or less. Y is O, S or NH), $-(CH_2)_{h15}-(CH=CH)-(CH_2)_{h14}-(N=N)-(CH_2)_{h13}-Y-(CH_2)_{h12}-$ (h12, h13, h14 and h15 are, respectively, the same or different integer of 0 to 7. But, the sum of h12, h13, h14 and h15 is 7 or less), (9) $-(CH_2)_{j1}-Y^1-(CH_2)_{j2}-Y^2-(CH_2)_{j3}-$ (j1, j2 and j3 are, respectively, the same or different integer of 0 to 10. But, the sum of j1, j2 and j3 is 10 or less, preferably 1 to 10. $Y^1$ and $Y^2$ are, respectively, O, S or NH), $-(CH_2)_{j4}-Y^4-(CH_2)_{j5}-Y^5-(CH_2)_{j6}-Y^6-(CH_2)_{j7}-$ (j4, j5, j6 and j7 are, respectively, the same or different integer of 0 to 9. But, the sum of j4, j5, j6 and j7 is 9 or lower. $Y^4$, $Y^5$, $Y^6$ and $Y^7$ are, respectively, O, S or NH), and so on. Specific examples of the divalent group include $-O-$, $-O-(CH_2)_{k1}-$ (k1 is an integer of 1 to 5, preferably 2 to 5), $-O-CH=CH-$, $-O-CH_2-CH=CH-$, $-O-CH=CH-CH_2-$, $-(CH_2)_{k1}-O-$ (k1 is an integer of 1 to 5, preferably 2 to 5), $-CH=CH-O-$, $-CH_2-CH=CH-O-$, $-CH=CH-CH_2-O-$, $-S-$, $-S-(CH_2)_{k2}-$ (k2 is an integer of 1 to 5, preferably 2 to 5), $-S-CH=CH-$, $-S-CH_2-CH=CH-$, $-S-CH=CH-CH_2-$, $-(CH_2)_{k1}-S-$ (k1 is an integer of 1 to 5, preferably 2 to 5), $-CH=CH-S-$, $-CH_2-CH=CH-S-$, $-CH=CH-CH_2-S-$, $-NH-$, $-NH-(CH_2)_{k2}-$ (k2 is an integer of 1 to 5, preferably 2 to 5), $-NH-CH=CH-$, $-NH-CH_2-CH=CH-$, $-NH-CH=CH-CH_2-$, $-(CH_2)_{k1}-NH-$ (k1 is an integer of 1 to 5, preferably 2 to 5), $-CH=CH-NH-$, $-CH_2-CH=CH-NH-$, $-CH=CH-CH_2-NH-$, $-(CH_2)_{k2}-$ (k2 is an integer of 1 to 5, preferably 2 to 5), —CH=CH—, —CH$_2$—CH=CH—, —CH=CH—CH$_2$—, —N=CH—, —CH=N—, —N=N—, —CH$_2$—N=CH—, —CH$_2$—CH=N—, —CH$_2$—N=N—, —N=CH—CH$_2$—, —CH=N—CH$_2$—, —N=N—CH$_2$— etc., and preferable examples include —O—(CH$_2$)$_{k1}$— (k1 is an integer of 1 to 5, preferably 2 to 5, more preferably 3 to 5), —S—(CH$_2$)$_{k2}$— (k2 is an integer of 1 to 5, preferably 2 to 5, more preferably 3 to 5), —NH—(CH$_2$)$_{k2}$— (k2 is an integer of 1 to 5, preferably 2 to 5, more preferably 3 to 5), —(CH$_2$)$_{k2}$— (k2 is an integer of 1 to 5, preferably 2 to 5, more preferably 3 to 5), —(CH$_2$)$_{k1}$—O— (k1 is an integer of 1 to 5, preferably 2 to 5, more preferably 3 to 5), —(CH$_2$)$_{k1}$—S—(k1 is an integer of 1 to 5, preferably 2 to 5, more preferably 3 to 5), and —(CH$_2$)$_{k1}$—NH— (k1 is an integer of 1 to 5, preferably 2 to 5, more preferably 3 to 5), and more preferable examples are —O—(CH$_2$)$_2$—, —O—(CH$_2$)$_3$—, —O—(CH$_2$)$_4$—, —O—(CH$_2$)$_5$—, —S—(CH$_2$)$_3$—, —S—(CH$_2$)$_4$—, —S—(CH$_2$)$_5$—, —NH—(CH$_2$)$_3$—, —NH—(CH$_2$)$_4$—, —NH—(CH$_2$)$_5$— and the like.

The divalent group may have substituent groups, and said substituent groups may be any group which can be bound to the divalent group, including, for example, a halogen atom, an optionally substituted amino group, an optionally substituted hydroxy group, an optionally substituted thiol group, an optionally substituted hydrocarbon group and an optionally substituted heterocyclic group exemplified as R$^1$ and R$^2$. Further, the substituent groups may be bound to each other to form a ring with the divalent group, and such rings include those exemplified as the rings formed by binding R$^1$ and R$^2$. Further, when an atom constituting the straight chain moiety is a sulfur atom in the "divalent group" represented by X above, the sulfur atom may be oxidized, and may be any of —S—, —SO— or —SO$_2$—.

Further, R$^1$ and a substituent group on X or R$^2$ and R$^3$ may be bound to each other to form an optionally substituted ring, and examples of such ring include those exemplified as the optionally substituted rings formed by binding R$^1$ and R$^2$. When R$^1$ and a substituent group on X are bound to each other to form an optionally substituted ring, a substituent group on the first to third (preferably the first to second, more preferably the first) atom in the straight chain moiety of X bound to the ethylene or vinylene is preferably bound to R$^1$.

Alternatively, a substituent group on the "ethylene" or "vinylene" of the "optionally substituted ethylene" or "optionally substituted vinylene" represented by W may be bound to a substituent group of X or R$^3$ to form an optionally substituted ring, and examples of such ring include those exemplified as the optionally substituted rings formed by binding R$^1$ and R$^2$. When a substituent group of the "ethylene" or "vinylene" and a substituent group of X are bound to each other to form a ring, binding between a substituent on the first to third (preferably first to second, more preferably first) atom in the straight chain moiety of X bound to the ethylene or vinylene and a substituent group of the "ethylene" or "vinylene" is preferable.

In the formula above, the combined line of "broken line and solid line" indicates a single bond or a double bond (preferably double bond).

When a compound having a substituent group is a basic compound depending on the kind of the substituent group exemplified above, the compound may be converted to a salt thereof by using an acid according to usual methods. Any acid may be used if the acid does not interfere with the reaction, and examples of the acid include inorganic acids such as hydrochloric acid, hydrobromic acid, phosphoric acid, sulfuric acid, nitric acid, sulfamic acid etc., organic acids such as formic acid, acetic acid, trifluoroacetic acid, tartaric acid, citric acid, fumaric acid, maleic acid, succinic acid, malic acid, p-toluenesulfonic acid, methanesulfonic acid, benzenesulfonic acid etc., and acidic amino acids such as aspartic acid, glutamic acid etc. When an obtained compound is a salt, the compound may be converted to a free base according to usual methods.

Alternatively, when a compound having a substituent group is an acidic compound depending on the kind of the substituent group exemplified above, the compound may be converted to a salt thereof by using a base according to usual methods. Any base may be used if the base does not interfere with the reaction, and examples of such salts include salts with inorganic bases, organic bases, basic amino acids, etc. Preferable examples of the salt with an inorganic base include alkali metal salts such as sodium salt, potassium salt, etc.; alkali-earth metal salts such as calcium salt, magnesium salt, etc.; and aluminum salt, ammonium salt, etc. Preferable examples of the salt with an organic base include salts with trimethylamine, triethylamine, pyridine, picoline, ethanolamine, diethanolamine, triethanolamine, dicyclohexylamine, N,N'-dibenzylethylenediamine, etc. Preferable examples of the salt with a basic amino acid include salts with arginine, lysine, ornithine, etc. When an obtained compound is a salt, the compound may be converted to a free acid according to usual methods.

The reaction above-mentioned (1) is conducted, for example, under a following reaction condition.

The compound represented by the formula:

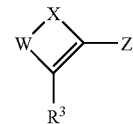

[wherein each symbol has the same meaning described above] or a salt thereof is produced by subjecting a compound represented by the formula:

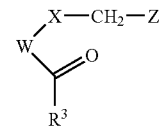

[wherein each symbol has the same meaning described above] or a salt thereof to cyclization reaction in a solvent containing carbonic diester.

The reaction above-mentioned (1) is preferably conducted in the presence of a base, and examples of such base include metal hydride compounds (e.g., alkali metal hydrides such as sodium hydride, potassium hydride, etc.), metal hydrocarbons (e.g., compounds having direct chemical bond between alkali metal and C$_{1-4}$ alkyl group such as n-butyl-lithium, etc.), alcoholates (e.g., compounds in which a hydroxy hydrogen of C$_{1-4}$ alcohols is replaced by a alkali metal such as sodium methoxide, sodium ethoxide, sodium t-butoxide, potassium methoxide, potassium ethoxide, potassium t-butoxide, lithium methoxide, lithium ethoxide, lithium t-butoxide, etc.), alkali metal hydroxides (e.g., NaOH, KOH, etc.), basic carbonates (e.g., alkali metal salts of carbonate such as sodium salt, potassium salt, etc., or alkali-earth metal salts of carbonate such as calcium salt, magnesium salt, etc.), basic bicarbonates (e.g., alkali metal salts of bicarbonate such as sodium salt, potassium salt, etc.), and organic bases (e.g., trimethylamine, triethylamine, diisopropylethylamine, pyridine, picoline, N-methylpyrrolidine, N-methylmorpholine, 1,5-diazabicyclo[4.3.0]non-5-ene, 1,4-diazabicyclo[2.2.2]octane, 1,8-diazabicyclo [5.4.0]-7-undecene, etc.), and preferably metal hydride compounds (e.g., sodium hydride, potassium hydride, etc.), alcoholates (e.g., NaOMe, NaOEt, t-BuONa, t-BuOK, etc.), particularly preferably alcoholates (e.g., NaOMe, NaOEt, t-BuONa, t-BuOK, etc.) is used.

The amount of base used for the reaction above-mentioned (1) is about 0.1 to 100 equivalents, preferably 1 to 5 equivalents.

The reaction solvent may be any solvent if only it contains carbonic diester, for example, a carbonic diester alone, a mixture of 2 or more carbonic diesters or a mixed solvent of carbonic diesters and a solvent except carbonic diesters.

The carbonic diester is a compound represented by the formula, Z"-O(CO)O-Z', [wherein, Z" and Z' each are an optionally substituted hydrocarbon group (preferably an optionally substituted alkyl group)]. Preferable are carbonic diesters which are liquid at the reaction temperature. In addition, Z" and Z' are preferably the same, and preferable examples of the carbonic diester are dialkyl carbonates, and di $C_{1-4}$ alkyl carbonates such as dimethyl carbonate, diethyl carbonate are preferably used.

The "solvent except carbonic diesters" used in combination with one or more kinds of carbonic diesters may be any solvent if the solvent does not interfere with the reaction, and includes, for example, halogenated solvents (e.g., methylene chloride, dichloroethane, chloroform, etc.), aliphatic hydrocarbons (e.g., n-hexane, etc.), aromatic hydrocarbons (e.g., benzene, toluene, etc.), ethers (e.g., tetrahydrofuran (THF), diethylether, etc.), polar solvents (e.g., dimethylformamide (DMF), dimethylsulfoxide (DMSO), etc.), alcohols (e.g., methanol, ethanol, propanol, isopropanol, n-butanol, 2-methoxyethanol, etc.), formic acid esters (e.g., $C_{1-4}$ alkyl formate, etc.), and oxalic acid diesters (e.g., di $C_{1-4}$ alkyl oxalate, etc), and preferably dimethylformamide (DMF), alcohols (e.g., methanol, ethanol, etc.) and so on.

The reaction may be conducted in an appropriate mixed solvent, preferably in a solvent containing carbonic diester (preferably, dimethyl carbonate or diethyl carbonate).

The reaction temperature is usually about −20 to 200° C., preferably about 10 to 100° C., and the reaction period is usually about 0.1 to 100 hours, preferably about 0.5 to 50 hours.

The reaction above-mentioned (7) is conducted, for example, under a following reaction condition.

The compound represented by the formula:

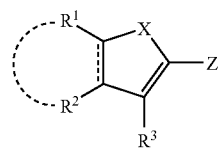

[wherein each symbol has the same meaning described above] or a salt thereof is produced by subjecting a compound represented by the formula:

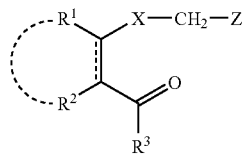

[wherein each symbol has the same meaning described above] or a salt thereof to a cyclization reaction in a solvent containing a carbonic diester.

The reaction above-mentioned (7) may be conducted under a similar condition to that for the reaction above-mentioned (1).

The reaction above-mentioned (13) is conducted for example under a following reaction condition.

The compound represented by the formula:

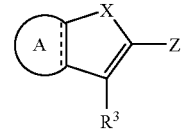

[wherein each symbol has the same meaning described above] or a salt thereof is produced by subjecting a compound represented by the formula:

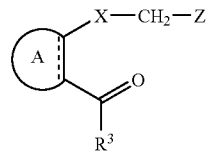

[wherein each symbol has the same meaning described above] or a salt thereof to a cyclization reaction in a solvent containing a carbonic diester.

The reaction above-mentioned (13) may be conducted under a condition similar to those for the reaction above-mentioned (1).

Among the compounds represented by the following formula:

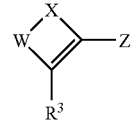

[wherein each symbol has the same meaning described above] or the salt thereof obtained in the reaction above-mentioned (1), the compounds represented by the formula:

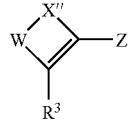

[wherein, Z is an electron-withdrawing group, W is an optionally substituted ethylene or an optionally substituted vinylene and when the ethylene or vinylene has two substituent groups, said substituent groups may be bound to each other to form an optionally substituted ring, $R^3$ is a hydrogen atom or an optionally substituted hydrocarbon group, and X" is a divalent group having 4 or more atoms in the straight-chain moiety thereof (preferably, a divalent group having 4, 5 or 6 atoms in the straight-chain moiety thereof)] or the salts thereof are novel compounds which have not been described in literature.

Further, the compounds represented by the formula:

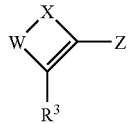

[wherein, each symbol has the same meaning described above] or a salt thereof obtained in the reaction above-mentioned (1) are useful as medicines, agricultural chemicals, foods, cosmetics and chemicals, or intermediates therefor. For example, from the compounds represented by the formula:

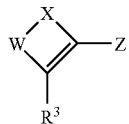

[wherein each symbol has the same meaning described above] or the salt thereof obtained in the reaction above-mentioned (1), useful medicines such as an osteogenesis promoter, a Na—H exchange inhibitor, treating agent for pollakiuria and incontinence of urine, edema treating agent and treating agent for central nervous system diseases can be produced according to the methods known in the art (e.g., methods described in JP-A 8-73476, WO99/55690, JP-A 11-302267, JP-A 11-302270, WO99/51242, etc.).

BEST MODE FOR CARRYING OUT THE INVENTION

Hereinafter, the present invention is described in more detail by the following Reference Examples and Examples, which are not intended to restrict the present invention.

EXAMPLES

Preparation of 2-alkoxybenzaldehyde Derivatives in General;

Reference Example 1

Ethyl 4-(2-Formylphenoxy)butyrate

Ethyl 4-bromobutyrate (6.6ml) was added to a suspension of salicyl aldehyde (5.0 g) and potassium carbonate (6.2 g) in DMF(15 ml), and the mixture was stirred at 90° C. for 1 hour. The mixture was allowed to cool to room temperature, and neutralized with 1N hydrochloric acid. After extraction with ethyl acetate, the organic layer was washed with saturated salt water, dried over anhydrous sodium sulfate, and concentrated. The concentrate was purified by silica gel column chromatography (n-hexane/ethyl acetate=4/1) and subsequent concentration of the appropriate eluate gave colorless oil of Ethyl 4-(2-formylphenoxy)butyrate (9.6 g, yield 99%).

$^1$H-NMR(CDCl$_3$, δ, 300 MHz): 1.27(3H, t, J=7.1 Hz), 2.14–2.23(2H, m), 2.54(2H, t, J=7.2 Hz), 4.11–4.18(4H, m), 6.96–7.04(2H, m), 7.52(1H, dt, J=1.7, 7.1 Hz), 7.82(1H, dd, J=1.7, 7.7 Hz), 10.49(1H, s).

IR(neat, cm$^{-1}$): 1733, 1687, 1598, 1243.

Compounds below in [REFERENCE EXAMPLE 2] to [REFERENCE EXAMPLE 4] were prepared according to a method similar to that of [REFERENCE EXAMPLE 1].

Reference Example 2

Ethyl 4-(4-Bromo-2-formyl phenoxy)butyrate

Colorless oil, yield 98%. $^1$H-NMR(CDCl$_3$, δ, 300 MHz): 1.23(3H, t, J=7.1 Hz), 2.11–2.20(2H, m), 2.50(2H, t, J=7.2 Hz), 4.08–4.16(4H, m), 6.85(1H, d, J=8.9), 7.58(1H, dd, J=8.9, 2.6 Hz), 7.88(1H, d, J=2.6 Hz), 10.37 (1H, s) IR(neat, cm$^{-1}$): 1731, 1683, 1590, 1272.

Reference Example 3

Ethyl 4-(2-Formyl-4-methoxy phenoxy)butyrate

Colorless oil, yield 99%. $^1$H-NMR(CDCl$_3$, δ, 300 MHz): 1.23(3H, t, J=7.1 Hz), 2.09–2.18(2H, m), 2.50(2H, t, J=7.2 Hz), 3.77(3H, s), 4.05–4.15(4H, m), 6.90(1H, d, J=9.1), 7.08(1H, dd, J=9.1, 3.2 Hz), 7.30(1H, d, J=3.2 Hz), 10.43 (1H, s). IR(neat, cm$^{-1}$): 1731, 1683, 1496, 1218.

Reference Example 4

Ethyl 5-(2-Formyl-4-methoxyphenoxy)pentanoate

Colorless oil, yield 99%. $^1$H-NMR(CDCl$_3$, δ, 300 MHz) 1.21(3H, t, J=7.1 Hz), 1.80–1.87(4H, m), 2.37(2H, t, J=7.1 Hz), 3.77(3H, s), 4.01–4.14(4H, m), 6.89(1H, d, J=9.1 Hz), 7.08(1H, dd, J=9.1, 3.2 Hz), 7.29(1H, d, J=3.2 Hz), 10.44 (1H, s). IR(neat, cm$^{-1}$): 1731, 1683, 1496, 1218.

Preparation of 2-formyl-N-methylaniline Derivatives in General

Reference Example 5

5-(4-Bromo-2-formyl-N-methylanilino)pentanoic Acid

A suspension of 1-methyl-2-piperidone (5.0 g) in 4N sodium hydroxide (22.1 ml) was heated and stirred for 8.5 hours under reflux. After the suspension was cooled to room temperature, conc. hydrochloric acid (7.4 ml) was added. A solution of sodium carbonate (9.4 g) and 5-bromo-4-fluorobenzaldehyde (4.5 g) in DMSO (74 ml) was added, and the resulting mixture was stirred for 1.5 hours under reflux. The mixture was allowed to cool to room temperature, and adjusted to pH of about 3.3 with 6N hydrochloric acid. After extraction with ethyl acetate, the organic layer was washed with saturated salt water, dried over anhydrous sodium sulfate, and concentrated. The precipitated crystal obtained was redissolved in isopropylether [IPE] (20 ml) under heating, and the solution was allowed to cool to room temperature, and stirred for 1 hour at 0° C. The crystal obtained was filtered and washed with IPE. Drying under reduced pressure (40° C., 1 hour) gave yellow crystal of 5-(4-bromo-2-formyl-N-methylanilino)pentanoic acid (4.0 g, yield 57%).

mp. 72–73° C. $^1$H-NMR (CDCl$_3$, δ, 300 MHz): 1.61–1.69 (4H, m), 2.36(2H, t, J=6.7 Hz), 2.87(3H, s), 3.13(2H, t, J=6.9 Hz), 6.97(1H, d, J=8.8 Hz), 7.54(1H, dd, J=8.8, 2.5 Hz), 7.86(1H, d, J=2.5 Hz), 10.17(1H, s). Anal. Calcd for C$_{13}$H$_{16}$NO$_3$Br: C,49.70; H,5.13; N,4.46; Br,25.43, Found: C,49.75; H,5.16; N,4.45; Br,25.40. IR(KBr, cm$^{-1}$): 1731, 1648.

Compounds below in [REFERENCE EXAMPLE 6] to [Reference EXAMPLE 8] were prepared according to a method similar to that of [REFERENCE EXAMPLE 5].

Reference Example 6

5-(2-Formyl-N-methylanilino)pentanoic Acid

Yellow oil, yield 37%. $^1$H-NMR(CDCl$_3$, δ, 300 MHz): 1.64–1.73(4H, m), 2.38(2H, t, J=6.7 Hz), 2.90(3H, s), 3.17 (2H, t, J=6.9 Hz), 7.04–7.13(2H, m), 7.50(1H, dd, J=1.7, 5.5 Hz), 7.80(1H, dd, J=1.7, 7.7 Hz), 10.28(1H. s). IR(neat, cm$^{-1}$): 1708, 1683.

Reference Example 7

5-(2-Formyl-4-nitro-N-methylanilino)pentanoic Acid

Yellow crystal, yield 93%. mp. 107–108° C. $^1$H-NMR (CDCl$_3$, δ, 300 MHz): 1.60–1.67(2H, m), 1.75–1.81(2H, m), 2.38(2H, t, J=6.7 Hz), 2.90(3H, s), 3.43(2H, t, J=7.4 Hz), 6.98(1H, d, J=9.4), 8.20(1H, dd, J=9.4, 2.8 Hz), 8.58(1H, d, J=2.8 Hz), 9.67(1H, s). IR (KBr, cm$^{-1}$): 1704, 1677, 1598, 1324, 1307.

Reference Example 8

6-(4-Bromo-2-formyl-N-methylanilino)hexanoic Acid

Yellow crystal, yield 80%. mp. 95–96° C. $^1$H-NMR (CDCl$_3$, δ, 300 MHz): 1.27–1.32(2H, m), 1.54–1.66(4H, m), 2.31(2H, t, J=7.4 Hz), 2.83(3H, s), 3.08(2H, t, J=7.5 Hz), 6.93(1H, d, J=8.8 Hz), 7.50(1H, dd, J=8.8, 2.5 Hz), 7.83(1H, d, J=2.5 Hz), 10.12(1H, s). Anal. Calcd for C$_{14}$H$_{18}$NO$_3$Br: C,51.23; H,5.53; N,4.27; Br,24.35. Found: C,51.25; H,5.54; N,4.21; Br,24.48. IR (KBr, cm$^{-1}$): 1720, 1644.

Preparation of 2-formyl-N-benzylaniline Derivatives in General

Reference Example 9

5-(4-Bromo-2-formyl-N-benzylanilino)pentanoic Acid

To a solution of benzaldehyde (6.0 g) in methanol (80 ml), 4-aminobutyric acid (6.6 g) and 1N sodium hydroxide (56.5 ml) were added. 20% Pd—C(wet, 0.6 g) was added to the reaction apparatus which was previously purged with an argon gas. Subsequently, the apparatus was filled with a hydrogen gas, and the solution was stirred at room temperature overnight. Pd—C was filtered off and washed with methanol. To the filtrate was added 6N hydrochloric acid (9.4 ml), and the solvents were evaporated. Subsequently, sodium carbonate (12.0 g) and DMSO/water (57 ml/37 ml) were added to the residue, and the resulting mixture was heated under reflux with dropwise addition of a solution of 5-bromo-4-fluorobenzaldehyde (5.7 g) in DMSO (17 ml), and stirred further for 5 hours. After cooled to room temperature, the solution was adjusted to pH of about 3.5 by addition of 6N hydrochloric acid. After extraction with ethyl acetate, the organic layer was washed with saturated salt water, dried over anhydrous sodium sulfate, and concentrated. The concentrate was purified by silica gel column chromatography (n-hexane/ethyl acetate=4/1) and subsequent concentration of the appropriate eluate gave yellow oil of 5-(4-bromo-2-formyl-N-benzylanilino)pentanoic acid (7.4 g, yield 61%).

$^1$H-NMR(CDCl$_3$, δ, 300 MHz): 1.52–1.65(4H, m), 2.27–2.35(2H, m), 3.08–3.15(2H, m), 4.31(2H, s), 7.01(1H, d, J=8.7 Hz), 7.16–7.36(5H, m), 7.57(1H, dd, J=8.7, 2.4 Hz), 7.92(1H, d, J=2.4 Hz), 10.36(1H, s). EI-MS(M*): 391. IR(neat, cm$^{-1}$): 1708, 1683.

A compound below in [REFERENCE EXAMPLE 10] was prepared according to a method similar to that of [REFERENCE EXAMPLE 9].

Reference Example 10

5-(4-Bromo-2-formyl-N-benzylanilino)heptanoic Acid

Yellow oil, yield 27%. $^1$H-NMR(CDCl$_3$, δ, 300 MHz): 1.21–1.26(4H, m), 1.46–1.56(4H, m), 2.27(2H, t, J=7.4 Hz), 3.05(2H, t, J=7.5 Hz), 4.26(2H, s), 6.97(1H, d, J=8.7 Hz), 7.13–7.28(5H, m), 7.51(1H, dd, J=8.7, 2.5 Hz), 7.87(1H, d, J=2.5 Hz), 10.30(1H, s). IR (neat, cm$^{-1}$): 1706, 1683.

Cyclization Reactions in General (Method A)

Example 1

2,3-Dihydro-1-benzoxepin-4-carboxylic acid ethylester

To a solution of 4-(2-formylphenoxy)butyric acid ethylester (2.4 g) in diethyl carbonate (24 ml), a solution of 20% sodium ethoxide in ethanol (4.1 g) was added at room temperature, and the solution was stirred at 50° C. for 1 hour. The solution was allowed to cool to room temperature, and neutralized with 1N hydrochloric acid. After ethyl acetate extraction, the organic layer was washed with saturated salt water, dried over anhydrous sodium sulfate, and concentrated. The concentrate was purified by silica gel column chromatography (n-hexane/ethyl acetate=10/1) and concentration of the appropriate eluate gave colorless oil of 2,3-dihydro-1-benzoxepin-4-carboxylic acid ethylester (1.3 g, yield 61%).

$^1$H-NMR(CDCl$_3$, δ, 300 MHz): 1.36(3H, t, J=7.1 Hz), 2.97–3.00(2H, m), 4.26–4.31(4H, m), 6.96–7.04(2H, m), 7.21–7.27(1H, m), 7.32–7.35(1H, m), 7.58(1H, s). IR (neat, cm$^{-1}$): 1700, 1249.

Reference Example 11

2,3-Dihydro-1-benzoxepin-4-carboxylic Acid Ethylester

To a solution of 4-(2-formylphenoxy)butyric acid ethylester (2.4 g) in THF (24 ml), potassium t-butoxide (1.2 g) was added at room temperature, and the mixture was stirred at 50° C. for 2 hours. The solution was allowed to cool to room temperature, and neutralized with 1N hydrochloric acid. After ethyl acetate extraction, the organic layer was washed with saturated salt water. The organic layer was subjected to HPLC analysis.

The results of quantitative analyses: 4-(2-formylphenoxy)butyric acid ethylester (0.1 g, yield 4%), 4-(2-formylphenoxy)butyric acid (0.3 g, yield 14%), 2,3-dihydro-1-benzoxepin-4-carboxylic acid ethylester (0.4 g, yield 17%), 2,3-dihydro-1-benzoxepin-4-carboxylic acid (0.3 g, yield 15%).

Compounds below in [EXAMPLE 2] to [EXAMPLE 4] were prepared according to a method similar to that of [EXAMPLE 1].

Example 2

7-Bromo-2,3-dihydro-1-benzoxepin-4-carboxylic Acid Ethylester (Method A)

White crystal, yield 34%. mp. 85–86° C. $^1$H-NMR (CDCl$_3$, δ, 300 MHz): 1.34(3H, t, J=7.1 Hz), 2.92–2.97(2H, m), 4.19–4.25(4H, m), 6.82(1H, d, J=8.6 Hz), 7.28(1H, dd, J=8.6, 2.4 Hz), 7.42(1H, d, J=2.4 Hz), 7.43(1H, s).

Example 3

7-Methoxy-2,3-dihydro-1-benzoxepin-4-carboxylic Acid Ethylester (Method A)

White crystal, yield 82%. mp. 62–63° C. $^1$H-NMR (CDCl$_3$, δ, 300 MHz): 1.32(3H, t, J=7.1 Hz), 2.92–2.95(2H, m), 3.76(3H, s), 4.17–4.28(4H, m), 6.77–6.81(2H, m), 6.87 (1H, dd, J=1.6, 7.4 Hz), 7.49(1H, s).

Example 4

8-Methoxy-3,4-dihydro-2H-1-benzoxocin-5-carboxylic Acid Ethylester (Method A)

Colorless oil, yield 11%. $^1$H-NMR(CDCl$_3$, δ, 300 MHz): 1.44(3H, t, J=7.1 Hz), 1.82–1.88(2H, m), 2.66–2.70(2H, m), 3.86(3H, s), 4.24–4.39(4H, m), 6.77 (1H, d, J=3.0 Hz), 6.92(1H, dd, J=3.0, 8.9 Hz), 7.02(1H, d, J=8.9 Hz), 7.70(1H, s). IR (neat, cm$^{-1}$): 1704, 1496, 1243.

Cyclization Reactions in General (Method B)

Example 5

8-Bromo-1-methyl-1,2,3,4-tetrahydro-1-benzazocin-5-carboxylic Acid Methylester

To a solution of 5-(4-bromo-2-formyl-N-methylanilino) pentanoic acid (3.0 g) in DMF(8 ml), potassium carbonate (1.6 g) and a solution of methyl iodide/DMF (1.6 g/2 ml) were added at room temperature, and the resulting mixture was stirred for 2 hours. Ethyl acetate and water were added to the mixture, and the organic layer was separated, washed with water, dried over anhydrous sodium sulfate, and concentrated to give yellow oil of 5-(4-bromo-2-formyl -N-methylanilino)pentanoic acid methylester (3.0 g, yield 97%).

$^1$H-NMR(CDCl$_3$, δ, 300 MHz): 1.58–1.64(4H, m), 2.28 (2H, t, J=6.8 Hz), 2.83(3H, s), 3.09(2H, t, J=6.8 Hz), 3.63(3H, s), 6.95(1H, d, J=8.8 Hz), 7.51(1H, dd, J=8.8, 2.4 Hz), 7,83(1H, d, J=2.4 Hz), 10.14(1H, s). FAB-MS ([M+ Na]$^+$): 350. IR(neat, cm$^{-1}$): 1735, 1681.

To a solution of 5-(4-bromo-2-formyl-N-methylanilino) pentanoic acid methylester (3.0 g) in dimethyl carbonate (40 ml), a solution of 28% sodium methoxide in methanol (2.3 g) was added at room temperature, and the resulting mixture was stirred at 50° C. for 2 hours. The mixture was allowed to cool to room temperature, and neutralized with 1N hydrochloric acid. After ethyl acetate extraction, the organic layer was washed with saturated salt water, dried over anhydrous sodium sulfate, and concentrated. The concentrate was purified by silica gel column chromatography (h-hexane/ethyl acetate=10/1) and the appropriate eluate was concentrated. The precipitated crystal was washed with IPE and collected by filtration. Drying under reduced pressure (40° C., 1 hour) gave yellow crystal of 8-bromo-1-methyl-1,2,3,4-tetrahydro-1-benzazocin-5-carboxylic acid methylester (0.9 g, yield 31%). mp. 88–89° C. $^1$H-NMR (CDCl$_3$, δ, 300 MHz): 1.44(2H, m), 2.54(2H, t, J=6.2 Hz), 2.87(3H, s), 3.42(2H, t, J=5.6 Hz), 3.78(3H, s), 6.56(1H, d, J=6.0 Hz), 7.19–7.23(2H, m), 7.68(1H, s). Anal. Calcd for C$_{14}$H$_{16}$NO$_2$Br: C,54.21; H,5.20; N,4.52; Br,25.76. Found: C,54.19; H,5.29; N,4.37; Br,25.74. IR(KBr, cm$^{-1}$): 1689, 1189.

Compounds below in [EXAMPLE 6] to [EXAMPLE 9] were prepared according to a method similar to that of [EXAMPLE 5].

Example 6

1-Methyl-1,2,3,4-tetrahydro-1-benzazocin-5-carboxylic Acid Methylester (Method B)

5-(2-Formyl-N-methylanilino)pentanoic acid methylester Yellow oil, yield 99%. $^1$H-NMR(CDCl$_3$, δ, 300 MHz): 1.58–1.68(4H, m), 2.30(2H, t, J=6.8), 2.86(3H, s), 3.12(2H, t, J=6.8 Hz), 3.64(3H, s), 7.01–7.10(2H, m), 7.46(1H, dt, J=1.7, 7.3 Hz), 7.76(1H, dd, J=1.7, 7.7 Hz), 10.25(1H, s). IR (neat, cm$^{-1}$): 1735, 1685, 1159.

1-methyl-1,2,3,4-tetrahydro-1-benzazocin-5-carboxylic Acid Methylester

Yellow crystal, yield 30%. mp. 80–82° C. $^1$H-NMR (CDCl$_3$, δ, 300 MHz): 1.42–1.50(2H, m), 2.57(2H, t, J=6.2 Hz), 2.90(3H, s), 3.45(2H, t, J=5.4 Hz), 3.79(3H, s), 6.62–6.73(2H, m), 7.11–7.22(2H, m), 7.80(1H, s). Anal. Calcd for C$_{14}$H$_1$NO$_2$: C,72.70; H,7.41; N,6.06. Found: C,73.00; H,7.65; N,6.06. IR (KBr, cm$^{-1}$): 1685, 1189.

Example 7

1-Benzyl-8-bromo-1,2,3,4-tetrahydro-1-benzazocin-5-carboxylic Acid Methylester (Method B)

5-(4-Bromo-2-formyl-N-benzylanilino)pentanoic Acid Methylester

Yellow oil, yield 100%. $^1$H-NMR(CDCl$_3$, δ, 300 MHz): 1.57–1.60(4H, m), 2.27(2H, t, J=6.7), 3.12(2H, t, J=6.6 Hz), 3.66(3H, s), 4.31(2H, s), 7.01(1H, d, J=8.7), 7.17–7.33(5H, m), 7.56(1H, dd, J=8.7, 2.5 Hz), 7.92(1H, d, J=2. 5 Hz), 10.35 (1H,s). EI-MS(M+): 403. IR (neat, cm$^{-1}$): 1735, 1683.

1-Benzyl-8-bromo-1,2,3,4-tetrahydro-1-benzazocin-5-carboxylic Acid Methylester

Yellow oil, yield 76%. $^1$H-NMR(CDCl$_3$, δ, 300 MHz): 1.44–1.50(2H, m), 2.59(2H, t, J=6.1 Hz), 3.50(2H, t, J=5.3 Hz), 3.81(3H, s), 4.45(2H, s), 6.50(1H, d, J=9.0), 7.09–7.39 (7H, m), 7.75(1H, s). EI-MS(M$^+$): 385.

IR(neat, cm$^{-1}$): 1704, 1495, 1087.

Example 8

9-Bromo-1-methyl-2,3,4,5-tetrahydro-1H-1-benzazonin-6-carboxylic Acid Methylester (Method B)

6-(4-Bromo-2-formyl-N-methylanilino)hexanoic Acid Methylester

Yellow oil, yield 98%. $^1$H-NMR(CDCl$_3$, δ, 300 MHz): 1.20–1.30(2H, m), 1.51–1.61(4H, m), 2.24(2H, t, J=7,4), 2.81(3H, s), 3.05(2H, t, J=6.6 Hz), 3.61(3H, s), 6.91(1H, d, J=8.8 Hz), 7.47(1H, dd, J=8.8, 2.3 Hz), 7.80(1H, d, J=2.3 Hz), 10.10(1H, s). FAB-MS([M+Na]$^+$): 364. IR(neat, cm$^{-1}$): 1735, 1681.

9-Bromo-1-methyl-2,3,4,5-tetrahydro-1H-1-benzazonin-6-carboxylic Acid Methylester Yellow oil, yield 18%. $^1$H-NMR-(CDCl$_3$, δ, 300 MHz): 1.67–1.77(2H, m), 1.87–1.96(2H, m), 2.30(2H, t, J=6.9 Hz), 2.76(3H, s), 3.12(2H, t, J=6.9 Hz), 3.77(3H, s), 6.70(1H, d, J=6.4 Hz), 7.19–7.22(2H, m), 7.60(1H, s). EI-MS(M$^+$):323. IR(neat, cm$^{-1}$): 1708, 1494.

Cyclization Reactions in General (Method C)

Example 9

8-Nitro-1-methyl-1,2,3,4-tetrahydro-1-benzazocin-5-carboxylic Acid Methylester

To a solution of 5-(2-formyl-4-nitro-N-methylanilino) pentanoic acid (3.0 g) in DMF (8.1 ml), potassium carbonate (1.6 g) and a solution of methyl iodide/DMF (1.8 g/1 ml) were added at room temperature, and the resulting mixture was stirred further for 2 hours. To the mixture, dimethyl carbonate (18 ml) and subsequently a solution of 28% sodium methoxide in methanol (5.0 g) were added and the resulting mixture was stirred at 50° C. for 2.5 hours. The mixture was allowed to cool to room temperature, and neutralized with 1N hydrochloric acid. After ethyl acetate extraction, the organic layer was washed with saturated salt water, dried over anhydrous sodium sulfate, and concentrated. The concentrate was redissolved in hot isopropyl alcohol [IPA], and the solution was allowed to cool to room temperature, stirred at room temperature further for 1 hour, and at ice temperature for 0.5 hours. The precipitated crystal was collected by filtration, and washed with IPA. The crystal was purified by silica gel column chromatography (n-hexane/ethyl acetate=2/1 to 1/1), and subsequent concentration of the appropriate eluate gave yellow crystal of 8-nitro-1-methyl-1,2,3,4-tetrahydro-1-benzazocin-5-carboxylic acid methylester (2.3 g, yield 78%). mp. 127–129° C. $^1$H-NMR (CDCl$_3$, δ, 300 MHz): 1.38–1.72(2H, m), 2.35–2.80(2H, m), 3.02(3H, s), 3.42–3.85(2H, m), 3.80(3H, s), 6.65(1H, d, J=9.4 Hz), 7.80(1H, s), 7.99–8.06(2H,m). Anal. Calcd for C$_{14}$H$_{16}$N$_2$O$_2$: C,60.86; H,5.84; N,10.14. Found: C,60.79; H,5.81; N,9.98. IR (KBr, cm$^{-1}$): 1708, 1255, 1191.

A compound below in [EXAMPLE 10] was prepared according to a method similar to that of [EXAMPLE 9].

Example 10

1-Benzyl-10-bromo-1,2,3,4,5,6-hexahydro-1-benzazecin-7-carboxylic Acid Methylester (Method C)

Yellow oil, yield 6%. $^1$H-NMR(CDCl$_3$, δ, 300 MHz): 1.24–1.29(2H, m), 1.44–1.50(2H, m), 1.57–1.63(2H, m), 2.13(2H, t, J=6.5 Hz), 2.89(2H, t, J=6.2 Hz), 3.48(3H, s), 3.90(2H, s), 7.02(1H, d, J=8.6 Hz), 7.10–7.25(6H, m), 7.37(1H, dd, J=8.6, 2.4 Hz), 7.48(1H, s). IR(KBr, cm$^{-1}$): 1712, 1279, 1232.

Reference Example 11

Preparation of 4'-ethoxy-4-hydroxy-1,1'-biphenyl-3-carbaldehyde

To a suspension of magnesium (0.5 g) in THF (7 ml), a solution of 1-bromo-4-ethoxybenzene (4.0 g) in THF (2.5 ml) was added slowly at room temperature under an argon atmosphere, and the resulting solution was stirred for 1 hour. Subsequently, a solution of trimethoxyborane (2.1 g) in THF (2.5 ml) was added dropwise at −10 to 10° C., and after further addition of THF (7 ml), the reaction mixture was stirred at the same temperature for 1 hour. The reaction mixture was allowed to warm to room temperature and tetrakistriphenylphosphine palladium (115mg), 5-bromo-2-hydroxybenzaldehyde (2.0 g) and an aqueous solution of tripotassium phosphate (11.1 g) in water (15 ml) were added, and the resulting mixture was stirred under reflux for 1 hour. After the mixture was allowed to cool to room temperature, 6N hydrochloric acid (20 ml) was added dropwise, and then toluene(20 ml) was added. After separation, the aqueous phase was further extracted with toluene (30 ml). The organic layers were combined and washed with aqueous 10% sodium chloride solutions (10 ml×3), dried over anhydrous magnesium sulfate and concentrated. The concentrate was purified by silica gel chromatography (n-hexane/ethyl acetate=6/1), and the appropriate eluate was concentrated. Diisopropylether (15 ml) was added to the concentrate and the resulting mixture was heated under reflux, and then allowed to cool to room temperature. n-Hexane (15 ml) was added to the solution, and stirred at room temperature for 1 hour and at 0° C. for 0.5 hour. The precipitated crystal was collected by filtration and washed with diisopropylether/n-hexane (1/1.4 ml) which was previously cooled to 0 to 5° C. Drying under reduced pressure (room temperature, 2 hours) gave yellow crystal of the title compound (1.8 g, yield 73%).

mp. 94–95° C.

Anal Calcd. for C$_{15}$H$_{14}$O$_3$: C,74.36; H,5.82. Found: C,74.61; H,5.80.

IR(KBr, cm$^{-1}$): 1660, 1473, 1276, 1245, 1047, 831.

$^1$H-NMR(CDCl$_3$, 300 MHz) δ 1.44(3H, t, J=7.0 Hz), 4.07(2H, q, J=7.0 Hz), 6.96(2H, dd, J=1.9, 6.7 Hz), 7.04(1H, d, J=8.4 Hz), 7.45(2H, dd, J=1.9, 6.7 Hz), 7.68–7.77(2H, m), 9.95(1H, s), 10.95(1H, s).

Reference Example 12

Preparation of 4-[(4'-ethoxy-3-formyl-1,1'-biphenyl-4-yl)oxy]butyric acid ethylester To a solution of 4'-ethoxy-4-hydroxy-1,1'-biphyenyl-3-carbaldehyde(1.0 g), and 4-bromobutyric acid ethylester (0.9 g) in DMF (5 ml) was added potassium carbonate (1.1 g) at room temperature, and the solution was stirred at room temperature for 14 hours, and at 50° C. for 3 hours. After the solution was allowed to cool to room temperature, water (10 ml) was added, and extracted with ethyl acetate (30 ml). The organic layer was washed with water (10 ml×3), and concentrated. To the concentrate was added diisopropylether (14 ml), and the resulting mixture was heated under reflux and subsequently cooled to room temperature. The solution was further stirred at room temperature for 1 hour, and at 0° C. for 1 hour. The precipitated crystal was collected by filtration and washed with diisopropylether (3 ml) which was previously cooled to 0 to 5° C. Drying under vacuum (room temperature, 2 hours) gave white crystal of the title compound (1.3 g, yield 91%). mp. 69–70° C.

Anal Calcd. for $C_{21}H_{24}O_5$: C,70.77; H,6.79. Found: C,70.91; H,7.08.

IR (KBr, cm$^{-1}$) 1683, 1606, 1471, 1270, 1240, 1187, 1047. $^1$H-NMR(CDCl$_3$, 300 MHz) δ 1.26(3H, t, J=7.1 Hz), 1.43(3H, t, J=7.0 Hz), 2.18–2.25(2H, m), 2.56(2H, t, J=7.1 Hz), 4.04–4.20(6H, m), 6.94(2H, dd, J=1.9, 6.7 Hz), 7.03 (1H, d, J=8.7 Hz), 7.47(2H, dd, J=1.9, 6.7 Hz), 7.72(1H, dd, J=8.7, 2.5 Hz), 8.02(1H, d, J=2.5 Hz), 10.53(1H, s).

Example 11

7-(4-Ethoxyphenyl)-2,3-dihydro-1-benzoxepin-4-carboxylic Acid Ethylester

To a solution of 4-[(41-ethoxy-3-formyl-1,1'-biphenyl-4-yl)oxy]butyric acid ethylester (0.50 g) in diethyl carbonate (5 ml) was added a solution of 20% sodium ethoxide in ethanol (0.57 g) at room temperature, and the mixture was then heated to 50° C. and stirred for 1 hour. The solution was neutralized with 1N hydrochloric acid, and extracted with ethyl acetate. The organic layer was washed, and concentrated. The concentrate was purified by silica gel chromatography (n-hexane/ethyl acetate=10/1) and subsequent concentration of the appropriate eluate gave white crystal of the title compound (0.39 g, yield 82%).

mp. 128–129° C. Anal Calcd. for $C_{21}H_{22}O_4$: C,74.54; H,6.55. Found: C,74.32; H,6.46.

IR(KBr, cm$^{-1}$), 1702, 1496, 1251, 1213.

$^1$H-NMR(CDCl$_3$, 300 MHz) δ 1.37(3H, t, J=7.1 Hz), 1.44(3H, t, J=7.0 Hz), 2.99–3.02(2H, m), 4.07(2H, q, J=7.0 Hz), 4.26–4.32(4H, m), 6.95(2H, dd, J=1.9, 6.7 Hz), 7.00 (1H, d, J=8.4 Hz), 7.41–7.51(4H, m), 7.65(1H, s).

INDUSTRIAL APPLICABILITY

The present invention provides a process suitable for mass production wherein cyclic compounds can be produced safely through a short step.

The invention claimed is:
1. A compound represented by the formula:

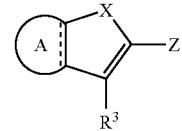

wherein Z is an electron-withdrawing group selected from the group consisting of
  a) a carboxyl group which may be optionally esterified,
  b) a group represented by the formula —(CO)NR$^{11}$R$^{12}$ wherein R$^{11}$ and R$^{12}$ are respectively a hydrogen atom or an optionally substituted hydrocarbon group, and R$^{11}$ and R$^{12}$ may be bound to each other to form a 5- to 7-membered cyclic amino group together with a neighboring nitrogen atom,
  c) a group represented by the formula —(CO)R$^4$ wherein R$^4$ is a hydrogen atom or an optionally substituted hydrocarbon group,
  d) nitrile group,
  e) nitro group,
  f) a group represented by the formula —(SO$_m$)R$^5$, wherein m is an integer of 1 or 2 and R$^5$ is an optionally substituted hydrocarbon group,
  g) a group represented by the formula —PR$^6$R$^7$ wherein R$^6$ and R$^7$ are each an optionally substituted hydrocarbon group,
  h) a group represented by the formula —(PO)(OR$^8$)(OR$^9$) wherein R$^8$ and R$^9$ each are a hydrogen or an optionally substituted hydrocarbon group,
  i) an optionally substituted aryl group,
  j) an optionally substituted alkenyl group,
  k) a halogen atom and
  l) a nitroso group;
ring A is an optionally substituted ring; the combined line of a broken line and and a solid line is a single bond or a double bond;
R$^3$ is a hydrogen atom or an optionally substituted hydrocarbon group; and
X is a divalent group is a straight-chain moiety of 4 or more atoms or a salt thereof.

2. 1-Benzyl-8-bromo-1,2,3,4-tetrahydro-1-benzazocin-5-carboxylic acid methyl ester.

* * * * *